United States Patent
Heo

(10) Patent No.: US 9,986,956 B2
(45) Date of Patent: Jun. 5, 2018

(54) IMAGE SENSOR AND ORAL SENSOR DEVICE USING SAME

(71) Applicants: Rayence Co., Ltd., Gyeonggi-do (KR); VATECH EWOO Holdings Co., Ltd., Gyeonggi-do (KR)

(72) Inventor: Sung-Kyn Heo, Gyeonggi-do (KR)

(73) Assignees: Rayence Co., Ltd., Gyeonggi-do (KR); VATECH EWOO Holdings Co., Ltd., Gyeonggi-do (KR)

( * ) Notice: Subject to any disclaimer, the term of this patent is extended or adjusted under 35 U.S.C. 154(b) by 0 days. days.

(21) Appl. No.: 15/502,769

(22) PCT Filed: Aug. 10, 2015

(86) PCT No.: PCT/KR2015/008347
§ 371 (c)(1),
(2) Date: Feb. 8, 2017

(87) PCT Pub. No.: WO2016/022005
PCT Pub. Date: Feb. 11, 2016

(65) Prior Publication Data
US 2017/0224296 A1    Aug. 10, 2017

(30) Foreign Application Priority Data

Aug. 8, 2014 (KR) ........................ 10-2014-0102293

(51) Int. Cl.
| | | |
|---|---|---|
| *A61B 6/00* | (2006.01) | |
| *A61B 6/14* | (2006.01) | |
| *A61C 19/04* | (2006.01) | |

(52) U.S. Cl.
CPC ............ *A61B 6/145* (2013.01); *A61B 6/14* (2013.01); *A61B 6/425* (2013.01); *A61C 19/04* (2013.01)

(58) Field of Classification Search
None
See application file for complete search history.

(56) References Cited

U.S. PATENT DOCUMENTS

| 4,734,034 A | 3/1988 | Maness et al. |
| 4,856,993 A | 8/1989 | Maness et al. |
| (Continued) | | |

FOREIGN PATENT DOCUMENTS

| EP | 1699232 A2 | 9/2006 |
| EP | 2213238 A1 | 8/2010 |
| (Continued) | | |

OTHER PUBLICATIONS

Korean Intellectual Property Office, International Search Report of International Application No. PCT/KR2015/008347, dated Nov. 6, 2015.

(Continued)

*Primary Examiner* — Hoon Song
(74) *Attorney, Agent, or Firm* — IP Legal Services, LLC

(57) ABSTRACT

The present invention provides an X-ray image sensor comprising: a sensor panel which is bendable, generates an electrical signal by detecting an X-ray, and has a first elasticity; a printed circuit board which transmits the electrical signal to the outside, has a second elasticity that is smaller than the first elasticity, and has a flexible property; and an elastic adjustment member which is made of an elastic material having a third elasticity that is larger than the first elasticity, and which adjusts the elasticity of the sensor panel and the printed circuit board so as to be greater than or equal to the third elasticity.

19 Claims, 4 Drawing Sheets

(56) References Cited

U.S. PATENT DOCUMENTS

| | | | |
|---|---|---|---|
| 6,042,267 | A | 3/2000 | Muraki et al. |
| 2003/0031296 | A1 | 2/2003 | Hoheisel |
| 2006/0028546 | A1 | 2/2006 | Kokkaliaris et al. |
| 2006/0067462 | A1 | 3/2006 | Hack |
| 2006/0262461 | A1 | 11/2006 | Wood |
| 2007/0053498 | A1* | 3/2007 | Mandelkern ............ A61B 6/145 378/184 |
| 2009/0034687 | A1 | 2/2009 | Ayraud |
| 2010/0072379 | A1* | 3/2010 | Nishino ................ G01T 1/2018 250/363.08 |
| 2010/0074401 | A1 | 3/2010 | Kayzerman |
| 2010/0220839 | A1 | 9/2010 | Takagi et al. |
| 2011/0013745 | A1 | 1/2011 | Zeller et al. |
| 2012/0291554 | A1* | 11/2012 | Baba .................... G01N 29/228 73/632 |

FOREIGN PATENT DOCUMENTS

| | | |
|---|---|---|
| JP | 2006-043465 A | 2/2006 |
| JP | 2006-521130 A | 9/2006 |
| JP | 2011-075390 A | 4/2011 |
| JP | 2013-015347 A | 1/2013 |
| KR | 20-0303670 Y1 | 2/2003 |
| KR | 20-0396821 Y1 | 9/2005 |
| KR | 20-2009-0001520 | 2/2009 |
| KR | 10-2014-0061177 A | 5/2014 |
| KR | 10-2014-0067257 A | 6/2014 |
| WO | 2009/138331 A1 | 11/2009 |

OTHER PUBLICATIONS

Korean Intellectual Property Office, Written Opinion of International Application No. PCT/KR2015/008347, dated Nov. 6, 2015.
Korean Intellectual Property Office, International Search Report of International Application No. PCT/KR2015/004658, dated Aug. 13, 2015.
Korean Intellectual Property Office, International Search Report of International Application No. PCT/2015/008348, dated Nov. 20, 2015.
Korean Intellectual Property Office, International Search Report of International Application No. PCT/KR2015/008349, dated Nov. 23, 2015.
Korean Intellectual Property Office, Written Opinion of International Application No. PCT/KR2015/008349, dated Nov. 23, 2015.
Korean Intellectual Property Office, Written Opinion of International Application No. PCT/KR2015/008348, dated Nov. 20, 2015.
European Patent Office, Extended European Search Report of EP Patent Application No. 15829636.8, Apr. 18, 2018.

\* cited by examiner

IMAGE SENSOR AND ORAL SENSOR DEVICE USING SAME

CROSS REFERENCE TO RELATED APPLICATIONS

This application is a National Stage Patent Application of PCT International Patent Application No. PCT/KR2015/008347 (filed on Aug. 10, 2015) under 35 U.S.C. § 371, which claims priority to Korean Patent Application No. 10-2014-0102293 (filed on Aug. 8, 2014), the teachings of which are incorporated herein in their entireties by reference.

TECHNICAL FIELD

The present invention relates to an image sensor and an oral sensor device using the same. More specifically, the present invention relates to an image sensor that is bendable to withstand external force and an oral sensor device that uses the same and is bendable within a predetermined bending limit to withstand counter force of an internal structure of a mouth when the oral sensor device is inserted into the mouth to capture an X-ray image and is brought into contact with the internal structure, applying physical force to the internal structure.

BACKGROUND ART

Film-based X-ray imaging had been used for medical and industrial applications for many years.

However, such film-based X-ray imaging is inefficient in terms of cost and time due to required development of an imaged film and difficulty of preservation of the developed film. To address this problem, X-ray imaging that uses a digital image sensor is currently being used instead of the film-based imaging.

A digital image sensor is generally made of a rigid material so as not to be bendable. This characteristic poses some problems according to imaging methods or usages.

For example, in an X-ray imaging process to obtain an X-ray image of an internal structure of the mouth, such as teeth and surrounding tissues, an image sensor is positioned in the mouth and an X-ray is irradiated to the internal structure. At this point, to obtain a cleaner X-ray image, the image sensor is brought into contact with and pressed against an internal structure in the mouth. Therefore, a patient has discomfort or pain.

To solve this problem, persons ordinarily skilled in the art have been researching an image sensor that is bendable within a predetermined bending limit.

At the present time, however, only a concept of a bendable image sensor is being discussed, and no specific technology to realize such a bendable image sensor has been presented in the field.

DISCLOSURE

Technical Problem

Accordingly, the present invention has been made keeping in mind the above problems occurring in the prior art, and an object of the present invention is to provide an image sensor that is bendable to resist external force within a predetermined bending limit and an oral sensor device using the same. When the oral sensor device is inserted into the mouth to capture an X-ray image of an internal structure of the mouth, the oral sensor device is bendable within a predetermined bending limit to withstand counter force of the internal structure, which is generated due to physical force applied to the internal structure by the X-ray image sensor and due to structural arrangement in the mouth.

Technical Solution

In order to accomplish the object of the invention, according to one aspect, there is provided an X-ray image sensor including: a sensor panel configured to detect an X-ray and generate an electrical signal, wherein the sensor panel has a first elasticity and is bendable; a printed circuit board configured to transfer the electrical signal to an external element, have a second elasticity lower than the first elasticity, and be flexible; and an elasticity adjustment member that is made of an elastic material having a third elasticity higher than the first elasticity and controlling the elasticity of the printed circuit board to be higher than the third elasticity.

The sensor panel includes a substrate, a photoelectric conversion element formed on the substrate, and a scintillator layer formed on the photoelectric conversion element. The substrate may have a thickness of 30 to 70 μm. The X-ray image sensor may be brought into close contact with an internal structure in a mouth to image an X-ray image of the internal structure. The X-ray image sensor may have an extent of bending that varies according to positions of the X-ray image sensor in the mouth, due to physical force applied to the internal structure and counter force of the internal structure. In the X-ray image sensor, elasticity in a first direction that is any one of a major-axis direction and a minor-axis direction may be lower than elasticity in a second direction that is the other direction of the major-axis direction and the minor-axis direction. In the elasticity adjustment member has a first direction elasticity that is in any one of a major-axis direction and a minor-axis direction may be lower than a second direction elasticity that is in the other direction of the major-axis direction and the minor-axis direction. A ratio of the first direction elasticity to the second direction elasticity in the second direction may be in a range of 1:1.5 to 1:6. The elasticity adjustment member may be made of a complex resin including a reinforcement material and a resin. The reinforcement material may be a fiber reinforcement material. The elasticity adjustment member may have a thickness of 0.2 to 0.4 mm. The fiber reinforcement material may be a carbon fiber. The fiber reinforcement material may include: first threads that are arranged to extend along the first direction for a first density; and second threads that are arranged to extend along the second direction for a second density higher than the first density. The fiber reinforcement material may include first threads each arranged to extend along the first direction, and second threads each arranged to extend along the second direction, and the elasticity adjustment member may include a first thread layer composed of the first threads and a second thread layer composed of the second threads, the first thread layer being smaller in number than the second thread layer. The first direction may be a major-axis direction of the X-ray image sensor and the second direction may be a minor-axis direction of the X-ray image sensor. The elasticity adjustment member may be disposed between the sensor panel and the printed circuit board. The X-ray image sensor may further include: a first adhesive that is soft configured to bond the sensor panel and the elasticity adjustment member; and a second adhesive configured to bond the elasticity adjustment member and the printed circuit board, wherein the second adhesive is soft. At least one of the first adhesive and the second adhesive may be an optically clear adhesive (OCA). The printed circuit board may include: a panel connection pad connected to the sensor panel to receive the electrical signal; a cable connection pad connected to a cable to transfer the electrical signal to an external element; a conductive wiring pattern that connects the panel connection pad and the cable connection pad to each other; and a metal thin film that is formed in at least a portion of an area other than the panel connection pad, the cable connection pad, and the conductive wiring pattern.

According to another aspect, there is provided an oral sensor device including: an image sensor that is bendable and configured to detect an X-ray and generates an electrical signal; a flexible mold housing that covers an outer surface of the image sensor, wherein the oral image sensor device has an extent of bending that varies along positions in a mouth by a counter force of an internal structure to a physical force of the oral sensor device when the oral sensor device is inserted into the mouth to capture an X-ray image of the internal structure.

The image sensor may include a sensor panel that is bendable and generates an electrical signal, a printed circuit board that transfers the electrical signal to an external element and is flexible, and an elasticity adjustment member that is made of an elastic material and disposed between the sensor panel and the printed circuit board. The oral sensor device may further include a protective cover and a window cover that are disposed in the mold housing and which cover a front surface and a back surface of the image sensor, respectively. Then when the physical force is applied in a direction perpendicular to a longitudinal direction of the oral sensor device, from a center of a back surface that is the opposite side of the internal structure, the oral sensor device may be bent within a bending limit due to counter force of the internal structure attributable to arrangement of the internal structure, wherein the bending limit is an angle between two tangent lines that are tangential to maximum flexural points at respective ends of the oral sensor device and the angle is less than 90° or greater than 180°.

Advantageous Effects

According to the present invention, an image sensor has a stacked structure including a sensor panel that is thin so as to be bendable, an elasticity adjustment member made of an elastic material, and a printed circuit board that is flexible. Each element of the image sensor is bendable within a predetermined bending limit to resist external force. Therefore, the image sensor can alleviate patient's discomfort while minimizing image distortion, and enables an oral image sensor using the same to be realized.

By using an elasticity adjustment member in which elasticity in a major-axis direction is lower than that in a minor-axis direction, it is possible to realize an image sensor that is bendable within a predetermined bending limit and has a relatively better bending characteristic in the major-axis direction than that in the minor-axis direction, and to realize an oral sensor device using the same. Therefore, it is possible reduce patient's discomfort when the oral sensor device is inserted in the mouth.

Since the sensor panel, the elasticity adjustment member, and the printed circuit board are bonded to each other via a flexible adhesive, it is possible to effectively reduce tension stress between the elements. For this reason, it is possible to realize an image sensor and an oral sensor device that can maintain high reliability and stability through many repetitive bending operations.

MODE FOR INVENTION

Herein below, preferred embodiments of the present invention will be described in detail, with reference to the accompanying drawings.

Figure 1:
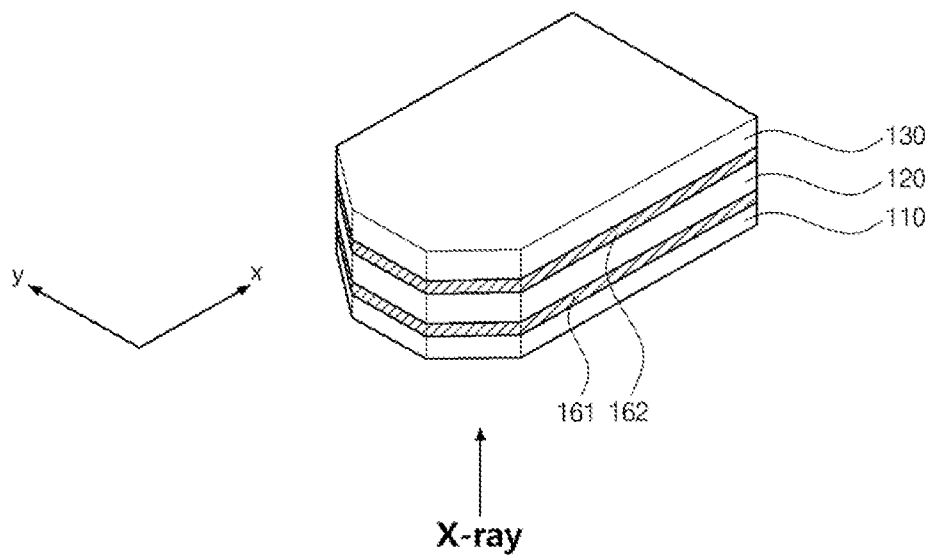
FIG. 1 is a perspective view that schematically illustrates an image sensor according to one embodiment of the present invention.

FIG. 1 is a perspective view that schematically illustrates an image sensor according to one embodiment of the present invention.

An image sensor 100 according to one embodiment of the present invention includes a sensor panel 110, an elasticity adjustment member 120, and a printed circuit board 130. The sensor panel 100, the elasticity adjustment member 120, and the printed circuit board 130 are preferably, but not limitedly, arranged in a scanning direction of an X-ray.

In the sensor panel 100 has an effective imaging area for obtaining an image. The effective imaging area includes a plurality of pixels arranged in rows and columns, i.e., in a matrix. Each pixel includes a photoelectric conversion element such as a photodiode, and a switching element, thereby converting incident light into an electrical signal and transmitting the electrical signal. Although not illustrated, pads for outputting the electrical signals are arranged on one side of the surface of the sensor panel 110. The switching elements may be transistors or thin film transistors (TFT).

For the image sensor 100 to be bendable, the sensor panel 110 is formed to be bendable. To achieve this, the sensor panel 110 may have a thickness of 100 or thinner when the sensor panel 110 is made of a brittle substrate such as semiconductor, ceramic, or glass substrate. Preferably, the sensor panel 110 may have a thickness of 30 to 70 μm. When the thickness of the sensor panel 110 is within the mentioned range, the sensor panel 110 has the optimum bending strength.

To form the sensor panel 110 having a thickness within the mentioned range, a method of eliminating the back surface of a raw substrate by a predetermined thickness is used. That is, the back surface of the raw substrate, which is opposite to the front surface on which the photoelectric conversion elements are formed, is subject to mechanical grinding, chemical polishing, plasma etching, or the like to obtain the sensor panel having the desired thickness.

The sensor panel 110 may be a direct conversion sensor panel that directly converts an incident X-ray into an electrical signal. Alternatively, the sensor panel 110 may be an indirection conversion sensor panel that first converts an incident X-ray into a visible ray and then converts the visible ray into an electrical signal.

Figure 2:
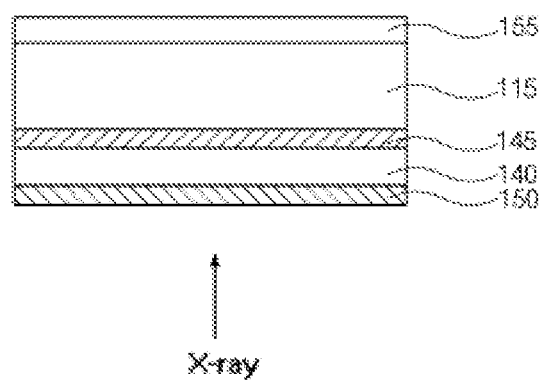
FIG. 2 is a cross-sectional view that schematically illustrates a cross section of a sensor panel according to the embodiment of the present invention.

When the sensor panel 110 is an indirect-conversion sensor panel 110, as illustrated in FIG. 2, the sensor panel 110 may be provided with a scintillator layer 140 that is formed on a first surface of the substrate 115, i.e., on the photoelectric conversion element. The scintillator layer 114 converts an X-ray into a visible ray.

FIG. 2 is a cross-sectional view that schematically illustrates the sensor panel according to one embodiment of the present invention.

With reference to FIG. 2, an incident surface of the sensor panel 110 is provided with the scintillator layer 140. Alternatively, the other surface that is opposite to the incident surface may be provided with the scintillator layer 140.

The scintillator layer 140 may be attached to the substrate 115, for example, via an adhesive 145. A transparent protective film 150 may be formed on the top surface of the scintillator layer 140 to protect the scintillator layer 140. The adhesive 145 may be a flexible adhesive with high optical transmittance. For example, the adhesive 145 may be an optically clear adhesive (OCA) film. The protective film 150 may be a resin film that is highly radiation-transmissive and moisture-repellant. For reference, the adhesive 145 may have a thickness of 10 to 50 μm to alleviate brittleness of the substrate. Preferably, the adhesive 145 may have a thickness of 15 to 40 μm on the assumption that the adhesive 145 is made of an OCA film.

On the other hand, the scintillator layer 140 is made of a fluorescent material, such as CsI, or Gadox ($Gd_2O_2$:Tb).

Here, since the image sensor 100 according to the present embodiment of the invention is made to be bendable, Gadox is preferable to CsI having a columnar crystal structure. Since Gadox takes the form of fine particles, even though the image sensor 100 is bent, Gadox is less likely to be broken and not cause defects. Moreover, the scintillator layer 140 made of Gadox has an advantage of easy manufacture.

For reference, the scintillator layer 140 made of Gadox may have a thickness of 250 to 500 μm to obtain sufficient intensity of light, and more preferably of 300 to 450 μm.

A surface of the substrate 115, opposite to the surface on which the scintillator layer 140 is formed, may be provided with a flexible layer 155. The flexible layer 155 may be made of resin that is flexible, for example, polyimide (PI). The flexible layer 155 may have a thickness sufficient to alleviate brittleness of the substrate 115 attributable to bending of the image sensor, thereby preventing the image sensor from being broken. For example, the flexible layer 155 may have a thickness of 50 to 150 μm.

With reference back to FIG. 1, the printed circuit board 130 is disposed on the back surface of the sensor panel 110 and electrically connected to a portion of the sensor panel 110, thereby receiving the electrical signal generated by the sensor panel 110 and transferring the electrical signal to an external element.

The printed circuit board 130 may be a so-called flexible printed circuit board that is made of a flexible material to make the image sensor 100 bendable.

Figure 3:
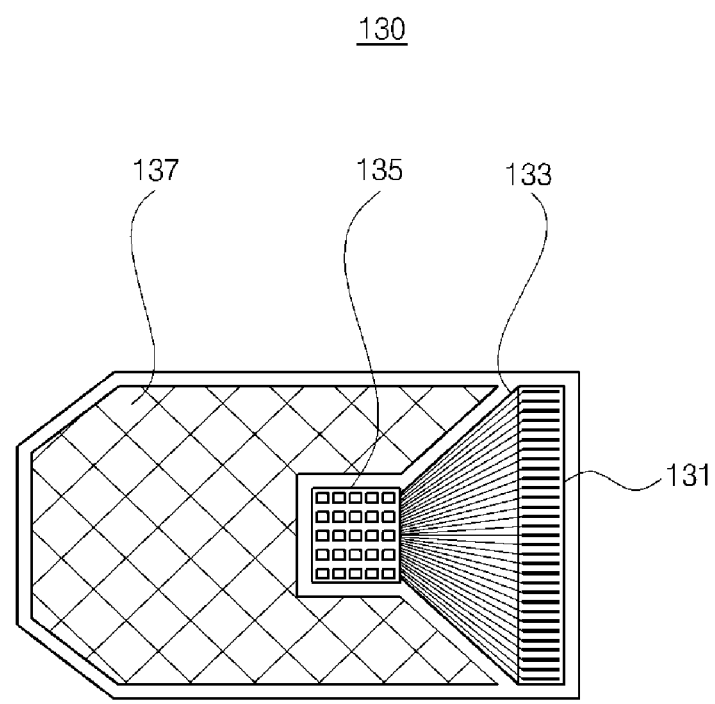
FIG. 3 is a plan view that schematically illustrates a printed circuit board according to the embodiment of the present invention.

With reference to FIG. 3 that is a plan view schematically illustrating the printed circuit board 130 according to the present embodiment of the invention, the printed circuit board 130 may include a panel connection pad 131, a conductive wiring pattern 133, and a cable connection pad 135.

As illustrated, the panel connection pad 131 is provided on one side of the surface of the printed circuit board and includes a plurality of pads. The pads of the panel connection pad 131 are electrically connected to pads formed on one side of the surface of the sensor panel 110 through wire bonding, soldering, or anisotropic conductive film (ACF) taping. The pads of the panel connection pad 131 receive the electrical signal generated by the sensor panel 110.

The conductive wiring pattern 133 includes a plurality of wiring patterns that connect the panel connection pad 131 and the cable connection pad 135 to each other. A first end of the wiring pattern is connected to the panel connection pad 131, thereby transferring the electrical signal applied from the sensor panel 110 to the cable connection pad 135 connected to a second end of the wiring pattern.

The cable connection pad 135 is connected to a transfer cable (herein below, refer to 210 of FIG. 7) to transfer the electrical signal to an external element. The transfer cable may be connected to the cable connection pad 135 in various ways. For example, connection can be made through soldering, plugging of connectors, taping of conductive films, and the like.

One surface of the printed circuit board 130 may be provided with the panel connection pad 131, the conductive wiring pattern 133, and a metal thin film 137 that is electrically insulated from the cable connection pad 135. The metal thin film 137 may be made of, for example, copper (Cu), but is not limited thereto.

The metal thin film 137 may be formed on at least a portion of an area other than the area in which the panel connection pad 131, the conductive wiring pattern 133, and the cable connection pad 135 are formed.

The metal thin film 137 may function as an earth means of the printed circuit board 130 or an electromagnetic interference (EMI) shielding means.

In addition, the metal thin film 137 may function as a means for controlling the bendable characteristic of the printed circuit board 130.

In the case in which there is no metal thin film 137, an area (second area) in which the panel connection pad 131, the conductive wiring pattern 133, and the cable connection pad 135 are formed, and the rest area (first area) exhibit different extents of bending. However, in the case that the metal thin film 137 is present, a difference in extent of bending between the areas is reduced. Therefore, with the metal thin film 137 being formed, the extent of bending of the printed circuit board 130 becomes substantially uniform over the entire range. By changing a material, area, and thickness of the metal thin film 137, it is possible to control the extent of bending of the printed circuit board 130.

In the present embodiment of the invention, the printed circuit board 130 having the same size as the sensor panel 110 is used. However, the printed circuit board 130 may have a smaller size than the sensor panel 110. The printed circuit board 130 may have a size that is substantially the same as the sum of areas of the panel connection pad 131, the conductive wiring pattern 133, and the cable connection pad 135. For reference, the preferred thickness of the printed circuit board 130 according to the present embodiment may be 150 to 350 μm but not limited thereto. The printed circuit board 130 may have a thickness at which the printed circuit board has elasticity equal to or lower than that of the sensor panel 110.

Figure 4:
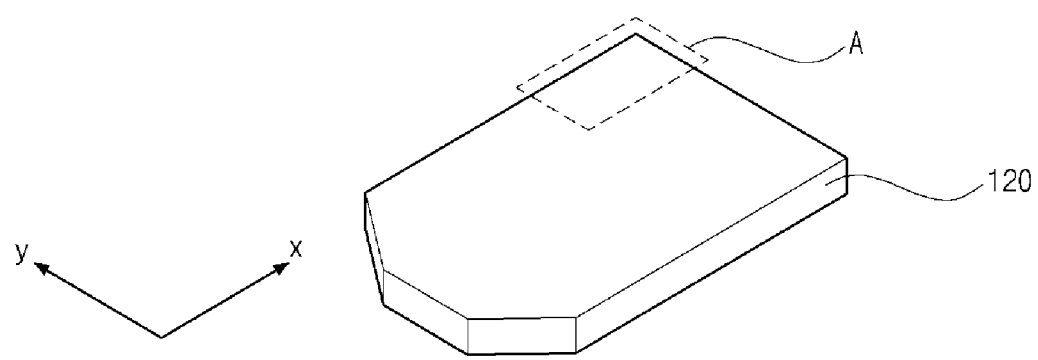
FIG. 4 is a perspective view that schematically illustrates an elasticity adjustment member according to the embodiment of the present invention.

FIG. 4 is a perspective view that schematically illustrates the elasticity adjustment member 120 according to the present embodiment of the invention. A description below will be given with reference to FIGS. 1 and 4.

The elasticity adjustment member 120 may be disposed between the sensor panel 110 and the printed circuit board 130 and have the same shape and size as the sensor panel 110 to cover the entire rear surface of the sensor panel 110. The elasticity adjustment member 120 is made of an elastic material having elasticity that is equal to or higher than that of the sensor panel 110 or the printed circuit board 130. The elasticity adjustment member 120 controls the extent of bending or the elasticity of the sensor panel 110 and the printed circuit board 130 such that the extent of bending of the sensor panel 110 and the printed circuit board 130 is equal to or lower than the extent of bending of the elasticity adjustment member 120, and the elasticity of the sensor panel 110 and the printed circuit board 130 is equal to or higher than the elasticity of the elasticity adjustment member 120. Therefore, the image sensor 100 can be bendable and elastically restorable within a range of elastic limit of the elasticity adjustment member and have a extent of bending that varies according to the intensity of an external impact. In addition, the elasticity adjustment member 120 functions to protect the sensor panel 110 not to be broken by alleviating the brittleness of the sensor panel 110 when the image sensor 100 is bent.

That is, the elasticity of each element may vary according to the size or thickness. However, when it is assumed that the sensor panel 110 has first elasticity and the printed circuit board 130 has second elasticity, under the presumption that the sensor panel 110 has the same structure and thickness shown in FIG. 2, the first elasticity is higher than the second elasticity. In addition, the elasticity adjustment member 120 is made of an elastic material having third elasticity that is equal to or higher than the first elasticity. That is, since the elasticity of the sensor panel 110 and the elasticity of the printed circuit board 130 are set to be equal to or higher than the third elasticity, the image sensor 100 can be bent to a degree within an elastic limit of the elasticity adjustment member 120 and can be elastically restored to its original form when external force is lifted after the image sensor 100 is bent within the elastic limit of the elasticity adjustment member due 120.

To accomplish this, the elasticity adjustment member 120 may be made of resin, and specifically made of a complex resin material composed of two or more materials. Preferably, the complex resin material may include a reinforcement material and a resin.

Preferably, the elasticity adjustment member 120 may be configured such that a bending characteristic in a first direction and a bending characteristic in a second direction perpendicular to the first direction are different when the first direction and the second direction are in the same plane.

Specifically, taking an example that the image 100 has a rectangular shape in which a length in an X-axis direction is longer than a length in a Y-axis direction in a plan view, it is preferable a bending characteristic in the X-axis direction (major-axis direction) of the elasticity adjustment member 120 is higher than that in the Y-axis direction (minor-axis direction). On the other hand, even when the image sensor 100 has a substantially square shape, the bending characteristic between the X-axis direction and the Y-axis direction is preferably different.

Such a bending characteristic makes the image sensor 100 bend better in the major-axis than in the minor-axis. This effectively alleviates patient's discomfort when the image sensor 100 is inserted into the mouth of a patient.

Specifically, corner portions of the image sensor 100 may cause discomfort when the image sensor 100 is used to capture an image of an internal structure in a patient's mouth. Especially, end portions of the image sensor 100 in the major-axis direction may cause the strongest discomfort. For this reason, by imparting a bending characteristic to the image sensor 100, specifically to end portions in the major-axis direction, it is possible to reduce patent's discomfort when the image sensor 100 is inserted into the patient's mouth.

In addition, since the bending characteristic in the X-axis direction (major-axis direction) of the elasticity adjustment member 120 is better than that in the Y-axis direction (minor-axis direction), it is necessary to distribute torsion stress to the X-axis direction and the Y-axis direction, and particularly to convert a majority part of the torsion stress to the X-axis direction stress, thereby preventing damage of the sensor panel 110 and specifically the substrate 115.

The elasticity adjustment member 120 having different bending characteristics according to directions in the same plane may be made of a complex resin material. For example, it may be made of fiber reinforced polymer (FRP) containing a fiber reinforced material. The FRP is a material in which inorganic fiber such as glass fiber, carbon fiber, or boron fiber or organic fiber such as aramid fiber, polyester fiber, or Kevlar fiber is added to a thermosetting resin base made of unsaturated polyester, epoxy, phenol, or polyimide or a thermoplastic resin base of polyamide, polycarbonate, ABS, PBT, PP, or SAN.

Next, the elasticity adjustment member 120 will be described in detail with reference to FIG. 5.

Figure 5:
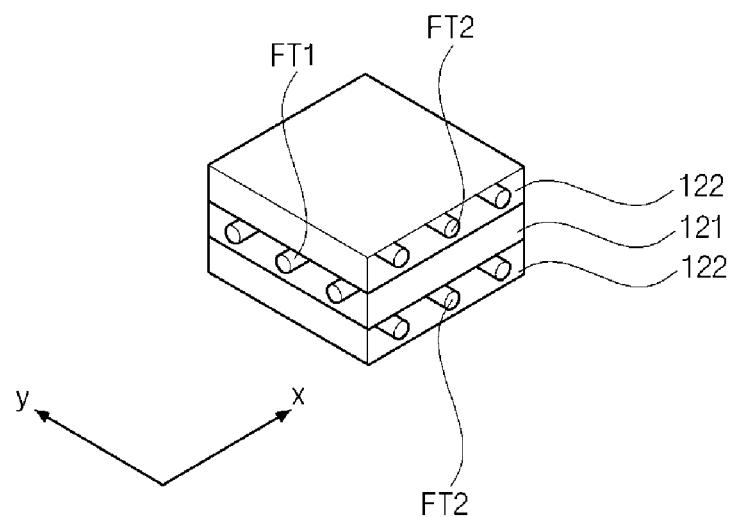
FIG. 5 is a partial expanded perspective view that schematically illustrates the elasticity adjustment member corresponding to a portion "A" of FIG. 4.

FIG. 5 is a partial expanded perspective view that schematically illustrates an "A" portion of the elasticity adjustment member 120. FIG. 5 illustrates a cross section of the elasticity adjustment member 120.

With reference to FIG. 5, in the elasticity adjustment member 120, first thread layers 121 and second thread layers 122 are alternately stacked and impregnated in respective resin layers; the first thread layer 121 being composed of first threads FT1 each extending along a first direction (X-axis direction) and the second thread 122 being composed of second threads FT2 each extending along a second direction (Y-axis direction). Each of the first and second threads FT1 and FT2 can be formed by aggregating and twisting the above-mentioned fiber in one direction.

In FIG. 5, the number of the first thread layers 121 in which the first threads FT1 are arranged to extend in the X-axis direction (major-axis direction) is smaller than the number of the second thread layers 122 in which the second threads FT2 are arranged to extend in the Y-axis direction (minor-axis direction). For convenience of explanation, FIG. 5 illustrates an example in which one first thread layer 121 and two second thread layers 122 are arranged. The first and second threads FT1 and FT2 are made from carbon fiber. Preferably, the elasticity adjustment member 120 according to the present embodiment is made of CFRP.

As described above, since the number of the first thread layers 121 with the first threads extending in the minor-axis direction is smaller than the number of the second thread layers 122 with the second threads extending in the long axis direction, the elasticity in the major-axis direction may be relatively lower than that in the minor-axis direction. That is, the bending characteristic in the major-axis direction is superior to that in the minor-axis direction.

Here, a ratio of the elasticity in the major-axis direction to the elasticity in the minor-axis direction is 1:1.5 to 1:6. The elasticity adjustment member 120 may be formed to have a thickness of 200 to 400 μm. When the elasticity adjustment member 120 has a thickness of 300 μm, the elasticity in the major-axis direction is preferably set to exhibit a bending strength of 1000 to 30000 MPa and the elasticity in the minor-axis direction is preferably set to exhibit a bending strength of 1500 to 180000 MPa. A bending strength within the mentioned range may be obtained even when the elasticity adjustment member has a thickness of 200 to 400 μm.

With the difference in the number of thread layers 121 and 122 in which arrangement directions of threads intersect each other, it is possible to form an elasticity adjustment member 120 that has a better bending characteristic in the major-axis direction than in the minor-axis direction.

Figure 6:
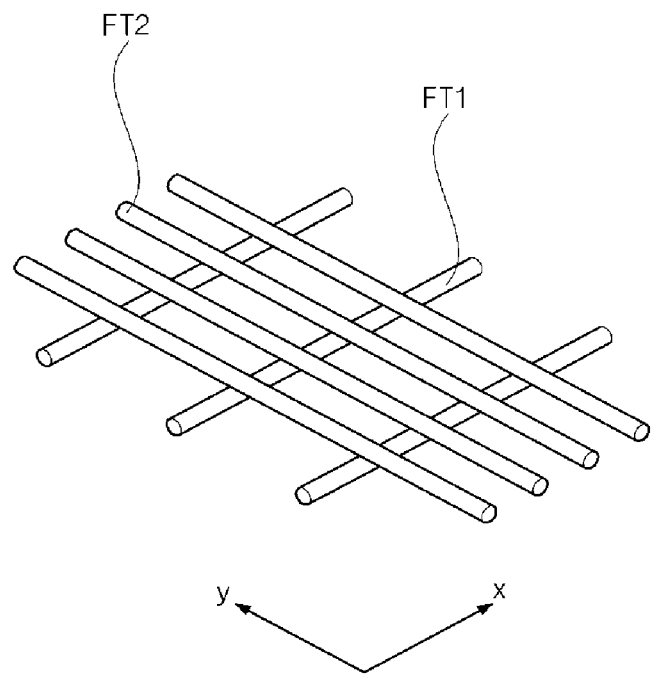
FIG. 6 is a partial expanded perspective view that schematically illustrates a portion of an elasticity adjustment member according to another embodiment of the present invention.

FIG. 6 is a partial expanded perspective view that schematically illustrates a portion of an elasticity adjustment member 120 according to another embodiment. First threads FT1 extending in X-axis direction are impregnated in a resin base to form a first thread layer and second threads FT2 extending in Y-axis direction are impregnated in a resin base to form a second thread layer. A density of first threads FT1 arranged to extend in the X-axis direction is lower than a density of second threads FT2 arranged to extend in the Y-axis direction. That is, a distance between adjacent first threads is longer than a distance between adjacent second threads. The first and second threads FT1 and FT2 are made of carbon fiber. According to the present embodiment, the elasticity adjustment member 120 is preferably made of CFRP.

As described above, since the density of the first threads FT1 extending in the major-axis direction is lower than the density of the second threads FT2 extending in the minor-axis direction, the major-axis direction has lower elasticity and a better bending characteristic than the minor-axis direction.

Just as the previous embodiment, a ratio of the elasticity in the major-axis direction to the elasticity in the minor-axis direction may be 1:1.5 to 1:6. The elasticity adjustment member 120 preferably has a thickness of 200 to 400 μm. When the elasticity adjustment member 120 has a thickness of 300 μm, the elasticity in the major-axis direction is set to exhibit a bending strength of 1000 to 30000 MPa and the elasticity in the minor-axis direction is set to exhibit a bending strength of 1500 to 180000 MPa. The bending strength within the mentioned range may be applied even when the thickness of the elasticity adjustment member is in a range of 200 to 400 μm.

As described above, with the difference in the density between the first threads FT1 and the second threads FT2 that intersect each other, it is possible to form the elasticity adjustment member 120 having a better bending characteristic in the major-axis direction than that in the minor-axis direction.

With reference to FIG. 1, the elasticity adjustment member 120 is bonded to both of the sensor panel 110 and the printed circuit board 130, provided to the front side and rear side thereof, via adhesives 161 and 162. For convenience of explanation, the adhesive 161 disposed between the elasticity adjustment member 120 and the sensor panel 110 is referred to as a first adhesive 161, and the adhesive 162 disposed between the elasticity adjustment member 120 and the printed circuit board 130 is referred to as a second adhesive 162.

The first and second adhesives 161 and 162 have good flexibility. For example, optically clear adhesive (OCA) may be used, but not limitedly, for the first and second adhesives 161 and 162.

With the use of the first and second adhesives 161 and 162 that both have good flexibility, it is possible to effectively alleviate interfacial stress and brittleness of the sensor panel when the image sensor 100 is bent.

In the present embodiment, since the sensor panel 110, the elasticity adjustment member 120, and the printed circuit board 130 are separate members having different characteristics, they are all different in tensile characteristics. Accordingly, when the image sensor 100 is bent, there exists a difference in displacement between those members, which causes tension stress. In this case, the flexible adhesives 161 and 162 disposed between those members effectively alleviate the tension stress.

Considering various characteristics and conditions, the first adhesive 161 preferably has a thickness of 30 to 70 μm and the second adhesive 162 preferably has a thickness of 10 to 50 μm.

As described above, the image sensor according to the present embodiment of the present invention includes the thin sensor panel 110, the elasticity adjustment member 120 made of an elastic material with elasticity higher than that of the sensor panel 110, and the printed circuit board 130 that is flexible. Since all these members are bendable, an image sensor that is bendable and which can alleviate patient's discomfort while minimizing image distortion can be realized.

Furthermore, since the elasticity adjustment member 120 in which the bending characteristic in the major-axis direction is better than that in the minor-axis direction is used, the image sensor 100 has a better bending characteristic in the major-axis direction than in the minor-axis direction, thereby alleviating patient's discomfort when inserted into a patient's mouth.

In addition, since the sensor panel 110, the elasticity adjustment member 120, and the printed circuit board 130 are combined by using the first and second adhesives 161 and 162, which are flexible and interposed between the sensor panel 110 and the elasticity adjustment member 120 and between the elasticity adjustment member 120 and the printed circuit board 130, the tension stress between these members having different characteristics can be effectively alleviated and high reliability and stability of the image sensor can be maintained even through repetitive bending operations of the image sensor.

Figure 7:
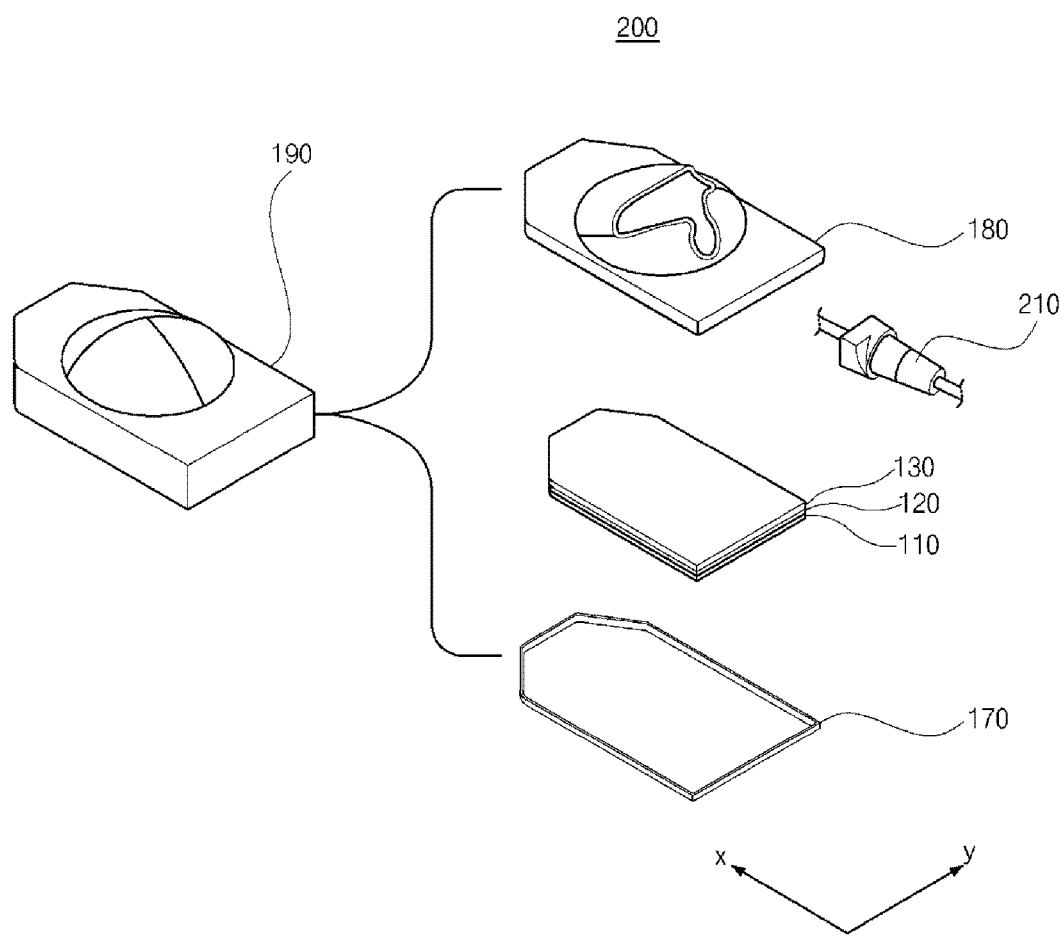
FIG. 7 is a perspective view illustrating an oral sensor device using the image sensor according to the embodiment of the present invention.

FIG. 7 is a perspective view illustrating an oral sensor device 200 using the image sensor according to the embodiment of the present invention.

An oral sensor device 200 according to one embodiment of the present invention includes the image sensor 110 described above, an elastic window cover 170 that covers a front surface (X-ray incidence surface) of the sensor panel 110, and an elastic protective cover 180 that covers a back surface of the printed circuit board 130. The oral sensor device 200 may further include a mold housing 190 that is flexible and covers an external surface of the image sensor 100. The mold housing 190 is separated from or combined with the window cover 170 and the protective cover 180. A transfer cable 210 used for signal transfer is connected to the printed circuit board 130 through the mold housing 190, or through the mold housing 190 and the protective cover 180.

The window cover 170 is made of a radiation-transmissive elastic material. For example, the window cover 170 may be made of flexible glass or FRP. The protective cover 180 is made of a material that has low elasticity and high rigidity. For example, the protective cover 180 may be made of polycarbonate (PC). The mold housing 190 is made of a radiation-transmissive, non-toxic, and flexible material. For example, the mold housing 190 may be made of a flexible material having a Shore hardness of about A30 to 50 such as silicone or urethane, but the material of the mold housing is not limited.

The material, thickness, and the like of the window cover 170, the protective cover 180, and the mold housing 190 may vary according to the desired bending characteristic of the oral sensor device. Preferably, when physical force that is perpendicular to the longitudinal direction of the oral sensor device is applied to a center of the back surface of an internal structure of the mouth when the oral sensor device is inserted to a patient's mouth to capture an X-ray image of the internal structure in the mouth; the oral sensor device according to the present embodiment is bent, due to counter force attributable to arrangement of the structure, within a bending limit that is an angle between tangent lines that are tangential to maximum flexural points at respective ends of the oral sensor device in the longitudinal direction of the oral sensor device, in which the angle is equal to or larger than 90° and smaller than 180°.

The oral sensor device 200 according to the embodiment of the present invention is brought into contact with an internal structure in a patient's mouth to capture an X-ray image of the internal structure (teeth or surrounding tissues) in the mouth.

The oral sensor device 200 according to the embodiment of the present invention has an extent of bending that varies according to physical force applied to the internal structure in the mouth and counter force of the internal structure. Accordingly, patient's discomfort is likely to be greatly reduced and image distortion is less likely to occur.

The invention claimed is:

1. An X-ray image sensor comprising:
   a sensor panel configured to detect an X-ray and generate an electrical signal, wherein the sensor panel has a first elasticity and is flexible;
   a printed circuit board configured to transfer the electrical signal to an external element, wherein the printed circuit board has a second elasticity lower than the first elasticity, and is flexible; and
   an elasticity adjustment member made of an elastic material having a third elasticity higher than the first elasticity and controlling the elasticity of the printed circuit board to be higher than the third elasticity,
   wherein the elasticity adjustment member has a first direction elasticity that is in any one of a major-axis direction and a minor-axis direction is lower than a second direction elasticity that is in the other direction of the major-axis direction and the minor-axis direction.

2. The X-ray image sensor according to claim 1, wherein the sensor panel includes a substrate, a photoelectric conversion element formed on the substrate, and a scintillator layer formed on the photoelectric conversion element.

3. The X-ray image sensor according to claim 2, wherein the substrate has a thickness of 30 to 70 μm.

4. The X-ray image sensor according to claim 1, wherein the X-ray image sensor is brought into close contact with an internal structure in a mouth to capture an X-ray image of the internal structure.

5. The X-ray image sensor according to claim 4, wherein the X-ray image sensor has an extent of bending that varies according to positions of the X-ray image sensor according to an applied force.

6. The X-ray image sensor according to claim 4, wherein in the X-ray image sensor, elasticity in a first direction that is any one of a major-axis direction and a minor-axis direction is lower than elasticity in a second direction that is the other direction of the major-axis direction and the minor-axis direction.

7. The X-ray image sensor according to claim 1, wherein a ratio of the first direction elasticity to the second direction elasticity is in a range of 1:1.5 to 1:6.

8. The X-ray image sensor according to claim 1, wherein the elasticity adjustment member is made of a complex resin including a reinforcement material and a resin.

9. The X-ray image sensor according to claim 8, wherein the reinforcement material is a fiber reinforcement material.

10. The X-ray image sensor according to claim 9, wherein the elasticity adjustment member has a thickness of 0.2 to 0.4 mm.

11. The X-ray image sensor according to claim 9, wherein the fiber reinforcement material is a carbon fiber.

12. The X-ray image sensor according to claim 9, wherein the fiber reinforcement material includes: first threads that are arranged to extend along the first direction for a first density; and second threads that are arranged to extend along the second direction for a second density higher than the first density.

13. The X-ray image sensor according to claim 9, wherein the fiber reinforcement material includes first threads each arranged to extend along the first direction, and second threads each arranged to extend along the second direction, wherein the elasticity adjustment member includes a first thread layer composed of the first threads and a second thread layer composed of the second threads.

14. The X-ray image sensor according to claim 6, wherein the first direction is a major-axis direction of the X-ray image sensor and the second direction is a minor-axis direction of the X-ray image sensor.

15. The X-ray image sensor according to claim 1, wherein the elasticity adjustment member is disposed between the sensor panel and the printed circuit board.

16. The X-ray image sensor according to claim 15, further comprising:
   a first adhesive configured to bond the sensor panel and the elasticity adjustment member, wherein the first adhesive is soft; and a second adhesive configured to bond the elasticity adjustment member and the printed circuit board, wherein the second adhesive is soft.

17. The X-ray image sensor according to claim 16, wherein at least one of the first adhesive and the second adhesive is an optically clear adhesive (OCA).

18. The X-ray image sensor according to claim 1, wherein the printed circuit board includes:
   a panel connection pad connected to the sensor panel to receive the electrical signal;
   a cable connection pad connected to a cable to transfer the electrical signal to an external element;
   a conductive wiring pattern connecting the panel connection pad and the cable connection pad to each other; and
   a metal thin film formed in at least a portion of an area other than the panel connection pad, the cable connection pad, and the conductive wiring pattern.

19. An X-ray image sensor comprising:
a sensor panel configured to detect an X-ray and generate an electrical signal, wherein the sensor panel has a first elasticity and is flexible;
a printed circuit board configured to transfer the electrical signal to an external element, wherein the printed circuit board has a second elasticity lower than the first elasticity, and is flexible; and
an elasticity adjustment member made of an elastic material having a third elasticity higher than the first elasticity and controlling the elasticity of the printed circuit board to be higher than the third elasticity,
wherein the elasticity adjustment member is made of a complex resin including a reinforcement material and a resin.

* * * * *